United States Patent
Rai et al.

(10) Patent No.: US 7,898,426 B2
(45) Date of Patent: Mar. 1, 2011

(54) ALERTNESS ESTIMATOR

(75) Inventors: Deepti Rai, Dorchester, MA (US);
Steven F. Kalik, Arlington, MA (US);
Setu Madhavi Namburu, Jamaica Plain, MA (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 335 days.

(21) Appl. No.: 12/243,055

(22) Filed: Oct. 1, 2008

(65) Prior Publication Data
US 2010/0079294 A1 Apr. 1, 2010

(51) Int. Cl.
*G08B 23/00* (2006.01)
(52) U.S. Cl. .................................. 340/575; 340/573.1
(58) Field of Classification Search ................. 340/575, 340/573.1; 600/301, 300, 544; 128/898, 128/920–925
See application file for complete search history.

(56) References Cited

U.S. PATENT DOCUMENTS

| | | | |
|---|---|---|---|
| 4,297,685 A | 10/1981 | Brainard, II | |
| 5,682,882 A | 11/1997 | Lieberman | |
| 5,813,993 A | 9/1998 | Kaplan et al. | |
| 6,313,749 B1 | 11/2001 | Horne et al. | |
| 6,496,724 B1 | 12/2002 | Levendowski et al. | |
| 6,553,252 B2 | 4/2003 | Balkin et al. | |
| 6,579,233 B2 * | 6/2003 | Hursh | 600/300 |
| 6,625,485 B2 | 9/2003 | Levendowski et al. | |
| 6,740,032 B2 * | 5/2004 | Balkin et al. | 600/300 |
| 6,743,167 B2 | 6/2004 | Balkin et al. | |
| 7,207,938 B2 * | 4/2007 | Hursh | 600/300 |
| 7,384,394 B2 * | 6/2008 | Hursh et al. | 600/300 |
| 7,766,827 B2 * | 8/2010 | Balkin et al. | 600/300 |

OTHER PUBLICATIONS

PDF downloaded from website entitled: http://www.theactigraph.com/index.php?option=com_docman&task=doc_details&Itemid=89&gid=2-2 (created on Jul. 22, 2008).
Acherman, P. et al., Simulation of daytime vigilance by the additive interaction of a homeostatic and circadian process, *Biological Cybernetics*, 71:115-121, 1994.

* cited by examiner

*Primary Examiner*—Toan N Pham
(74) *Attorney, Agent, or Firm*—Gifford, Krass, Sprinkle, Anderson & Citkowski, P.C.

(57) ABSTRACT

Example apparatus and methods for estimating a living being's alertness include modeling the sleep-wake cycle using a function generator circuit to model the circadian component, and one or more analog circuits to model the homeostatic and inertial components. In some embodiments of the present invention, temporal scaling is used for more rapid modeling, for example using time periods of seconds or less to represent an hour of the sleep-wake cycle.

27 Claims, 10 Drawing Sheets

ALERTNESS ESTIMATOR

FIELD OF THE INVENTION

The invention relates to apparatus and methods for estimating alertness.

BACKGROUND OF THE INVENTION

The safety and effectiveness of human activities can be improved by providing an estimate of the person's alertness. Hence, improved methods and apparatus for estimating alertness would be very useful.

SUMMARY OF THE INVENTION

Examples of the present invention relate to estimating a person's alertness, which may be expressed, for example, as a numerical parameter within an alertness range. The sleep-wake cycle of a person can be modeled in terms of circadian, homeostatic, and inertial components, and contributions from these components combined and used to provide the alertness estimate. The estimated alertness can be displayed, for example using a gauge or other visual representation of alertness. For example, an estimated alertness can be provided to the person in the form of a numerical parameter, for example between zero and 100, or as an alarm in cases where alertness is below a predetermined level. In some examples, the estimated alertness can be presented as a likelihood of sleep or absentmindedness, in which case a numerical parameter which increases with decrease in alertness is presented. In examples of the present invention, alertness may be estimated for any living being having a sleep-wake cycle, such as a person or other mammal (such as a horse, dog, or cat), or other living being.

Examples of the present invention include one or more analog electrical circuits used for modeling the sleep-wake cycle in the estimation of human alertness. An alertness estimate, for example in the form of a numerical parameter, facilitates behavior modification, for example allowing a person to modify their behavior to avoid hazardous conditions. Hence, the alertness estimate can improve personal safety and task selection.

An example apparatus for providing an alertness estimate comprises an electronic circuit including one or more analog circuit components for modeling the sleep-wake cycle. In some examples, the electronic circuit includes a first analog circuit for modeling the homeostatic component of the sleep-wake cycle, and a second analog circuit for modeling the inertial component of the cycle. The first analog circuit may be a resistor-capacitor (RC) circuit, and the second analog circuit may be a resistor-inductor (RL) analog circuit. For example, the homeostatic model circuit may include a resistor-capacitor circuit having a capacitive element, the homeostatic component being modeled by a potential difference across the capacitive element. The capacitive element may be provided by one or more individual capacitors. The capacitive element may be charged through a first resistive load and discharged through a second resistive load, and the first resistive load and the second resistive load may each be provided by a resistor or network of resistors. The capacitive element, first resistive load, the second resistive load may be adjustable, for example using external controls on a housing enclosing the electronic circuit, so as to increase modeling accuracy. For example, an adjustable resistance value may be provided using a voltage-tunable resistor, and/or by switchable selection of one or more resistors. Similar approaches may be used to adjust inductance or capacitance values.

The electronic circuit may also include a circadian modeling signal generator. Oscillatory signals may be used with components at various biologically relevant frequencies, for example 1 cycle/24 hours, 1 cycle/12 hours, 1 cycle/8 hours, or other period. Additional frequencies such as 1 cycle/365 days (Solar year) or 1 cycle/28 days (lunar month), or other frequencies may also be included. In some cases, sinusoidal components may be co-sinusoidal, for example depending on the chronotype being modeled (e.g. for morning people versus night people chronotype). In other examples, complex sinusoidal signals may be used, which allow greater freedom in modeling. An example electronic circuit may include at least first and second sine wave generators, where the first sine wave generator oscillates with an approximately 24 hour period, and the second sine wave generator oscillates with an approximately 12-hour period, the phases of these oscillators being selected independently. Additional sine wave generators with their own periods and phases may also be included, for example to improve modeling accuracy.

A non-inverting summing amplifier may be used to combine contributions from the circadian component, the homeostatic component, and the inertial component. The amplifier output may be used as an estimate of the alertness. The electronic circuit may further include a sleep-wake time input, receiving sensor signals correlated with the person's activity, such as activity or pulse rate sensors, and circuitry operable to determine transitions between a sleep cycle and a wake cycle. For example, a sleeping state may be determined from a low pulse rate, or minimal activity sensor signals for a predetermined time period, such as between 10 and 30 minutes.

The electronic circuit may receive sensor signals from one or more sensors, for example an activity sensor (such as an accelerometer, pedometer, and the like), light sensor, and the like. The person's activity may be used to determine transitions between a sleeping state and a waking state, allowing modeling of the homeostatic and inertial components with the first and second analog circuits.

In some examples, an apparatus comprises one or more sensors, for example one or more sensors selected from a group of sensors consisting of an activity sensor (such as an accelerometer), a position sensor, a light sensor, body temperature sensor, thermal sensor, pulse rate sensor, or EEG sensor. The electronic circuit may further receive circadian phase data, such as sunrise data, sunset data, manually entered data, ambient light data, or other data related to the person's circadian rhythm and influences thereon. An apparatus may further include a clock, so as to provide an estimate of the local time.

In some embodiments, an apparatus may include visual, audible, and/or haptic indicators of alertness level, which may provide a quantitative measure of estimated alertness, or in some cases may provide an alarm when the alertness level falls below one or more predetermined thresholds. Written tuning advice can be provided to accelerate individualization and customization for a modeled person. Tuning advice can be given to facilitate re-initialization in the event of incomplete or noisy data capture by the device or by outside sensors communicating with the device.

In further examples of the present invention, an apparatus may further include one or more user inputs, for example for entering data related to the alertness model, and optionally a parameter tuning input by which parameters used in the analog circuits may be adjusted. An apparatus may include a setup and/or reset circuit, by which circuit parameters can be initially determined, or returned to an original setting. An apparatus may further include visual indicators such as a display, bar graph, meter, and the like, and may include an audible alarm such as a buzzer. An apparatus may further include a communications unit, for example for communicating with a local or wide area network for exchange of relevant data.

Activity data from an activity sensor (such as an accelerometer) can be used to determine the state (asleep or awake) of a person, and associated transition times. A sleep-wake transition detection circuit can be used to detect transitions, and a clock can be used to associate times with the transitions, which may be stored in memory. Other physiological sensors can be used as an activity sensor, such as a pulse rate sensor, EEG sensor, respiratory sensor, and the like.

An apparatus may operate using temporal scaling or unscaled (real time) simulations. For temporal scaling, transition times can be stored as sleep-wake transition data for use during operation in a temporal scaling mode.

Either periodically, or on user request, stored sleep-wake transition data can be used to control the switching time during operation of the electronic circuit. A switch controller can be used to control the switch states in the model circuits, for example switch states being toggled in response to stored transition data. In real time operation, switch states may be responsive to detected sleep-wake transitions.

Alertness future estimates can be made by the apparatus assuming no additional change in the sleep wake state, for example assuming a person remains awake, and the circuit may predict when the estimated alertness crosses the warning threshold to trigger a warning. The time represented by the difference between the scaled warning time and the scaled present time reported (as an unscaled time) to indicate how long before alertness is predicted to fall to a dangerous level.

In real-time operation with no temporal scaling, the state of the switches in the homeostatic [RC] and inertial [RL] circuits can be toggled in response to detected sleep-wake transitions. The estimated alertness level tracks the alertness of the person. The reading of estimated alertness may be suppressed when a person is detected to be asleep. Alarms can be given at the time that the estimated alertness goes below the threshold for a warning, although a user may predict when that will happen based on their past experiences.

DETAILED DESCRIPTION OF THE PREFERRED EMBODIMENTS

Figure 1:
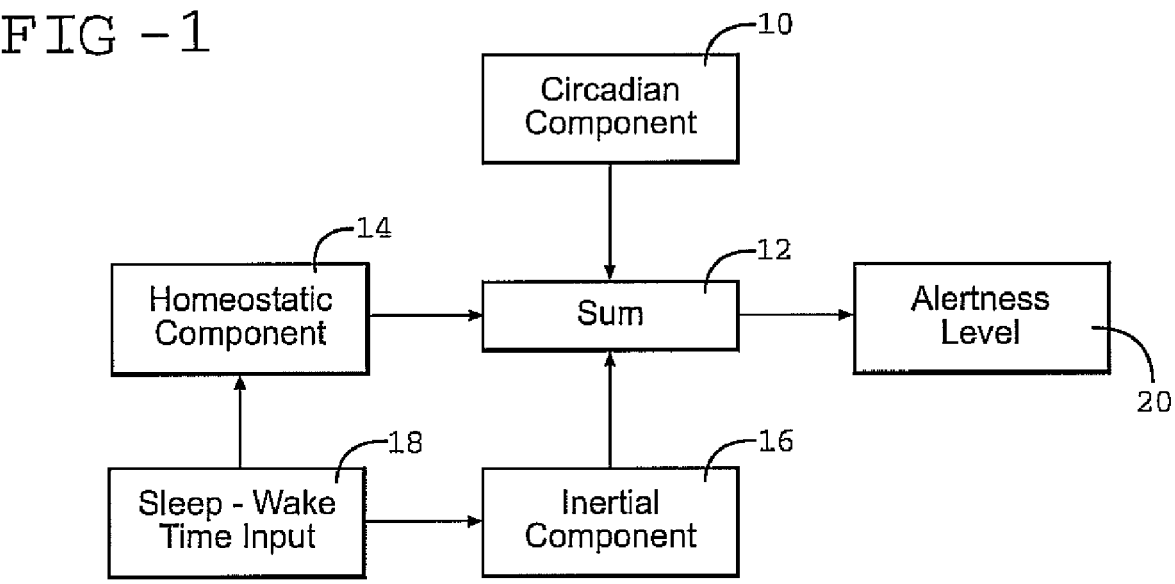
FIG. 1 shows a simplified schematic of an alertness estimator.

An example apparatus for determining a person's alertness has an electronic circuit which models the sleep-wake cycle, the electronic circuit including a model of the circadian component, an analog circuit for modeling the homeostatic component of the sleep-wake cycle, and/or an analog circuit for modeling the inertial component of the sleep-wake cycle. The circadian model represents the effect of light-dark changes on alertness, the homeostatic model represents the effect of previous periods of sleep and wakefulness on alertness, and the inertial model represents transient opposition to a sleep-wake status change. Circuit parameters may be determined using values for an average person, and an optional parameter tuning system (such as adjustable resistors) allows circuit parameters to be modified to improve the model representation for an individual modeled person.

Examples of the present invention detect the sleep-wake cycle of a person and use this to provide an estimate of the person's alertness. Feedback can be provided to the person in the form of a quantitative estimate, or as an alarm in the cases where alertness is below a predetermined level. Examples of the present invention include an analog electrical circuit in the estimation of human alertness, and provide an alertness estimate that enables a person to modify their behavior or task selections accordingly. Alertness data can facilitate personal safety, task effectiveness, and sensible task selection.

Embodiments of the present invention include analog electrical circuit elements that allow a portable device to be provided that is smaller and lighter than previous alertness estimators. Hence, embodiments of the present invention are well suited for portability, and may be carried by a person in the form of an apparatus supported by the person's body, such as a wrist-mounted device. The functions of embodiments of the present invention can be combined with other functionalities. For example, an alertness estimator according to an embodiment of the present invention may be combined with a cell phone, music player, PDA, heart rate monitor, energy expenditure monitor, pedometer, and/or other functionalities.

In some examples of the present invention, a current state of alertness is estimated and displayed to the person. In other examples, an alertness estimate for future times can be projected, allowing the person to modify their behavior if a low level of alertness is estimated for a future time, for example if an alertness level below a threshold value is estimated for a time for which alertness above the threshold value is desired.

An example apparatus comprises a user input (for example in the form of buttons or data entry ports), one or more sensors, an electrical circuit for providing an alertness estimate, a visual display, and an alarm. The visual display may be in the form of a meter, bar graph, or other visually discernable display, such as an electronic display. The alarm may be an audible alarm, flashing light, or other attention-getting mechanism by which a person may be warned of a low level of alertness, either at the present moment or within a predetermined future time interval. An apparatus may further include a tuning mechanism, for example a mechanism for tuning one or more analog circuits. For example the circuit may include an adjustable capacitor, variable resistor, and/or variable inductor that may be adjusted. An apparatus may provide a setup and tuning functionality, by which feedback provided by a person using a user input may be used to modify modeling parameters to increase the accuracy of the alertness estimator. Documentation recommends particular parameters to tune to customize the device.

An input may be provided for receiving data about the light/dark cycle of the local environment. In other examples, a light sensor may be used to determine such data. Further, sensors or input devices may be used to establish a recent history of sleep-wake times, allowing a current state of alertness to be estimated.

In a representative example, an electronic circuit provides an alertness estimate by modeling the overall alertness as a sum of three components. The first component is a circadian rhythm, which includes oscillatory components having 24 hour and 12 hour periods and potentially additional oscillatory periods as appropriate to match circadian rhythms of an individual person. The relative amplitudes of these components may be adjustable. Further, the period of the oscillatory components may further be adjustable around the approximately 24, 12, and other periodic components respectively, and this may be achieved by receiving input data or activity data from sensors for example. The phases of these oscillatory components may also be adjusted. The model further includes a homeostatic component and an inertial component. In a simplified explanation, the circadian component accounts for light and dark influence on alertness, the homeostatic component accounts for the effect of recent sleep and wakefulness, and the inertial component represents a transient opposition to the change in state from sleep to wakefulness and vice versa. An apparatus may be configured with typical parameters for average persons. However, an apparatus may further allow parameter tuning to personalize the model for an individual person.

An alertness level output combines the results of three estimation subsystems, and provides an alertness estimator to a display. The apparatus may include one or more displays, for example a gauge, a display screen, a bar graph, and the like. Displayed values may also include threshold values to which the present or future alertness may be compared. A person may receive a visual indication of the difference between a present alertness level and that which may present a hazard within a certain activity. If alertness falls below a threshold value, one or more alerts may be provided to the person.

In examples of the present invention, the homeostatic model comprises a first analog circuit, in particular a resistor-capacitor (RC) circuit. The RC circuit may comprise a capacitor, a first resistor through which the capacitor is charged, a second resistor through which the capacitor discharges, and switches activated by sleep-wake transitions (the term here including waking to sleeping transitions and sleeping to waking transitions). For example, the capacitor may be charged through the first resistor during a sleeping state, and discharged through the second resistor during a waking state. Hence, first and second RC time constants are used to describe the homeostatic component of the sleep-wake cycle. The first and second resistors may be independently adjusted.

Further, the inertial model may comprise a second analog circuit, in particular a resistor-inductor (RL) circuit. The RL circuit may comprise an inductor, a first resistor through which an inductive energy transient is stored, a second resistor through which inductive energy discharges, and one or more switches activated by a sleep-wake transition. For example, the inductive energy generation on closing of a first switch may provide a first transient signal on a sleep-wake transition, and a second transient signal on a wake-sleep transition. Hence, first and second RL time constants are used to describe the inertial component of the sleep-wake cycle. The first and second resistors may be independently adjusted.

In some examples of the present invention, the inertial component may be omitted from the modeling. In other examples, the effects of sleep-wake cycle history may be taken into account to modify the magnitude and shape of the inertial component.

The use of analog circuits allows the homeostatic and/or inertial modeling to be simplified. In previous examples, complex computer systems have been used to model the human sleep-wake cycle. However, a person may not wish to carry a computing device in order to receive the information related to alertness. By using a simple analog circuit for the homeostatic and/or inertial modeling, circuit complexity is vastly reduced. Further, simple adjustments of the RC and/or RL circuits may be used to adjust the model to increase accuracy in relation to a particular individual.

FIG. 1 is a simplified schematic of an electronic circuit used to model alertness. The circuit includes a circadian component model 10, a homeostatic component model 14, and an inertial component model 16. The results of these three component models are summed by the sum circuit 12, and the output of the sum circuit at 20 may be used as a representation of the person's alertness level. The schematic further includes a sleep-wake time input 18, for example provided by a sleep-wake transition circuit, which provides sleep-wake transition time data to the homeostatic component model and inertial component model. Sleep-wake transition data, for example time of sleep-wake transitions, may be provided by a sleep-wake transition circuit receiving user inputs and/or data from one or more sensors. Sensors may be part of the apparatus, or part of an external device in communication with the apparatus. Sleep-wake transition data may be entered by a user of the apparatus, for example using a data entry mechanism, and may be assumed based on the normal sleep patterns of a modeled person. The modeled person may be the same as the apparatus user. Sleep-wake transition data may be stored within a memory of the apparatus, and used in alertness estimation performed either in real time or in time scaled simulations, for present and future alertness estimation.

Figure 2:
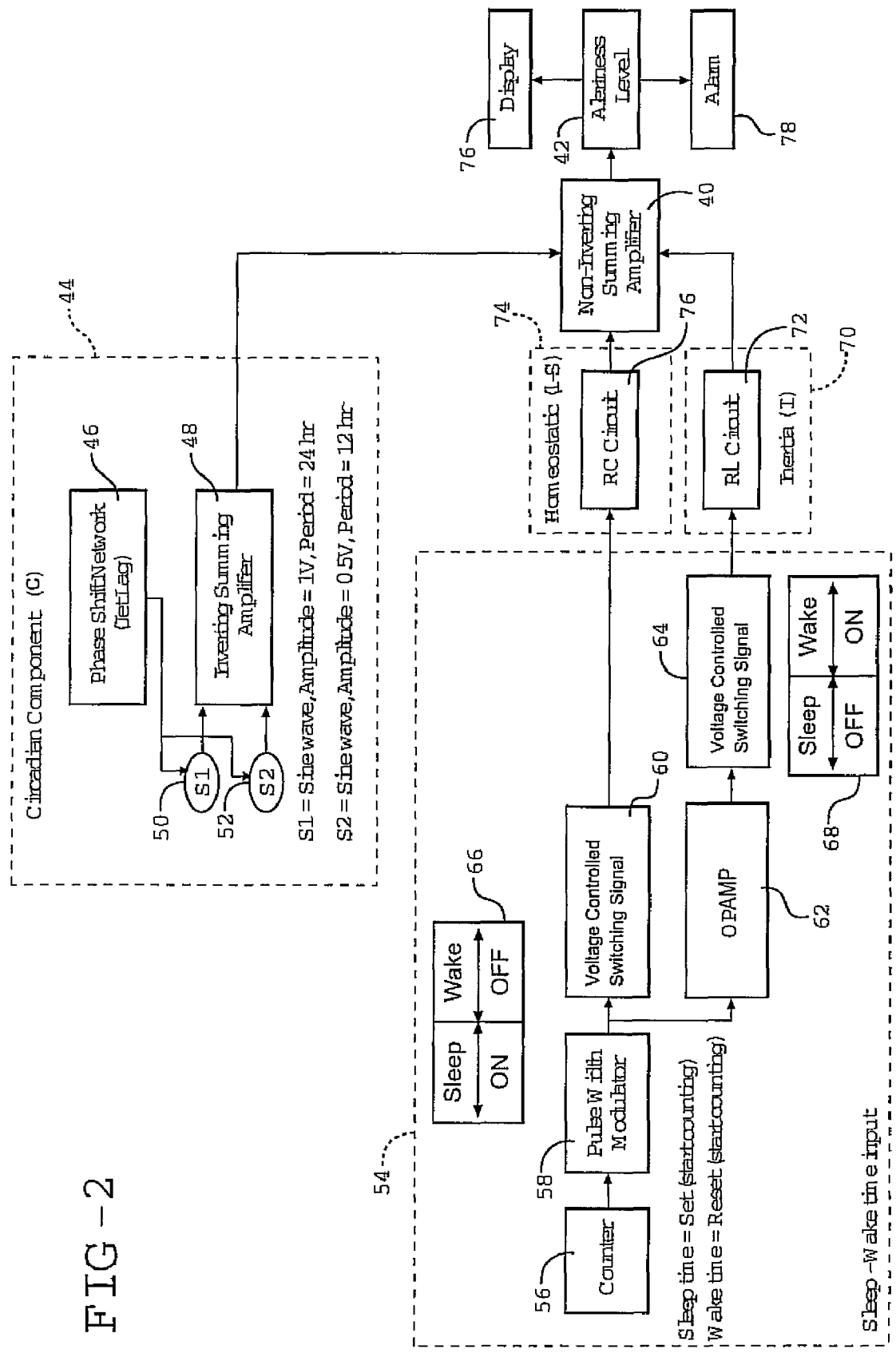
FIG. 2 shows a more detailed schematic of an alertness estimator.

FIG. 2 is a more detailed schematic of an example electronic circuit. The figure shows the circadian component model circuit generally at 44, the homeostatic model circuit at 74, and the inertial model circuit at 70. The sleep-wake time input circuit is shown generally at 54. The results of the three circuit models are received by non-inverting summing amplifier 40. The outputs from the circadian, homeostatic, and inertial model circuits are combined by the non-inverting summing amplifier, so as to output an estimated alertness at 42.

The alertness data is transmitted to a display 76 and an alarm 78. For example, an alarm may be given if the person's alertness has decreased below a threshold value. The display 76 may represent one or more visual displays. The alarm 78 may be any attention-getting mechanism, such as a flashing light, noise, vibration, and the like.

The circadian component model 44 is provided by a function generator circuit including a first sine wave oscillator 50 and a second sine wave oscillator 52. The first and second sine wave oscillations are received by inverting summing amplifier 48. A phase shift input 46 may be used to adjust the phases of the first and/or second oscillators, for example as may be necessary if the person changes time zone. For example, a position signal from a GPS, cellphone, or other position sensor may be used to determine the time zone and provide an input to the phase shift circuit. The electronic circuit further comprises a sleep-wake transition detection circuit, in this example sleep-wake time input circuit 54, which comprises counter 56, pulse width modulator 58, voltage control switch 60, inverting operational amplifier 62, and voltage control switch 64. In this particular example the counter starts when sleep is initiated, and resets on waking. Transitions between sleep and waking states are provided to the homeostatic model 74 and the inertial model 70. The waveform 68 illustrates an electronic waveform describing sleep-wake states and transitions between them. A sleep-wake transition circuit may receive sleep-wake data from user input, for example using a data entry mechanism, or receive data from one or more sensors, such as a light sensor, activity sensor, position sensor, and the like.

At the start of a sleep time, the counter is set and counts until the wake time, at which time the counter is reset. As long as the counter is set, the output of the Pulse Width Modulator (PWM) is high. The voltage controlled switch is on as long as the PWM output is high and will switch off when the PWM output is low (when the counter resets at wake time). Hence Sleep time=Counter set=Voltage controlled switch ON=capacitor charging/inductor energy storage (discussed further below), and Wake time=Counter reset=Voltage controlled switch OFF=capacitor discharging/inductor energy dissipation. Hence the sleep-wake time controls the charging and discharging of the capacitor and inductor. Other approaches may be used.

The circadian model may include light-dark related influences on alertness. For example, an apparatus according to the present invention may include a light sensor, clock, position sensor, sunrise and sunset data for the appropriate time zone, or other functionality allowing phase and/or amplitude modifications to be made to oscillatory components of the circadian model. The homeostatic model may include the effect of previous sleep and wakefulness in the model. The inertial mechanism transiently opposes the change of state from sleep to wakefulness or vice versa. Circuit parameters may be set for a typical person, and an optional parameter tuning system (such as adjustable resistors) allows circuit parameters to be modified to improve the model representation for an individual person.

The resulting alertness level, which combines outputs of the model circuit subsystems (and perhaps future subsystems as knowledge of the dynamics of these human systems grows over time) may be displayed using one or more display systems ranging from simple analog gauges to detailed graphical models in two dimensional displays. The values displayed can also include threshold values to which the alertness is compared to determine when to trigger one or more alarms to signal the alertness state to the person.

The system set-up and tuning advice allows customization of the device and initialization of the system.

Further detailed examples are discussed below. Temporal scaling was used, where 1 second in these model circuits represented one hour for a person. Component values are adjusted accordingly.

In some examples of the present invention, temporal scaling can be used to simulate alertness over a future period, such as one or more hours, or one or more days, in a matter of seconds or milliseconds, depending upon scaling factors used. This facilitates future planning, such as event or task scheduling.

Circadian Component

The circadian component can be modeled as a sum of two sine waves, having approximately 24 hour and 12 hour periods respectively. The relative amplitude of the 12 hour rhythm may be approximately 0.5. The two sine wave oscillators output to an inverting summing amplifier, and the output of the amplifier represents the circadian component.

A phase shift network can be incorporated to include the effect of jet lag on the circadian component. The circadian component can be phase shifted based on direction (advance/delay) and magnitude of the phase shift (due to travel to different time zones).

Figure 3A:
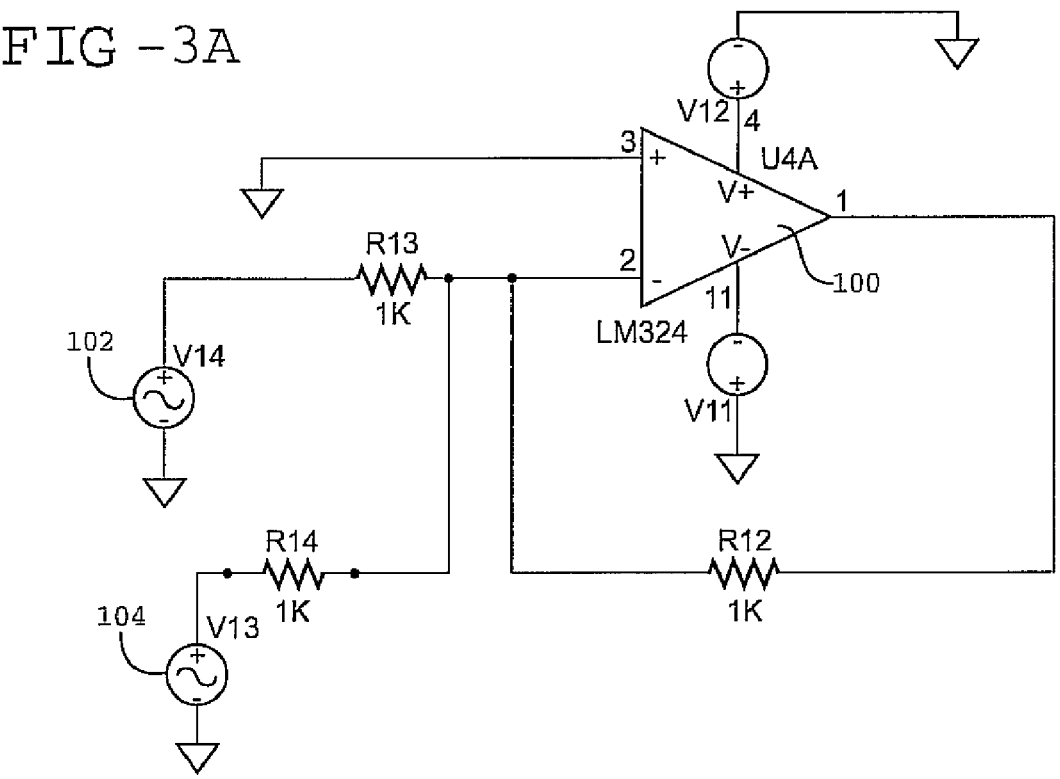
FIG. 3A shows a circuit for simulating the circadian component of alertness, including just first and second oscillators.

FIG. 3A shows a circuit for a function generator that can be used to provide an output representative of the circadian component of the sleep-wake cycle. The circuit includes first sine wave oscillator 102 and second sine wave oscillator 104. The sine wave oscillations are combined and amplified by operational amplifier (op-amp) 100. Hence, the circuit may be very simply implemented.

Figure 3B:
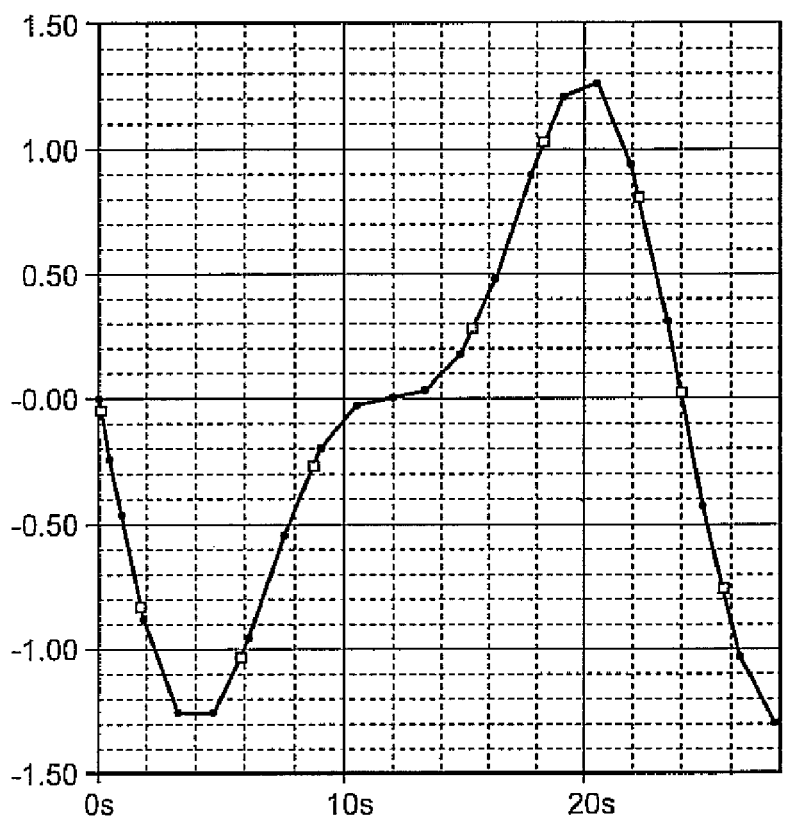
FIG. 3B is a typical output from the circuit of FIG. 3A.

FIG. 3B represents a typical output of the circuit of FIG. 3A. In this example, the circadian component includes contributions from the two oscillations, having periods of 12 hours and 24 hours respectively. In this example, the simulation is run over a time scale of 1 second representing 1 hour. However, the simulation could also be run over other time periods, in particular shorter time periods (such as over milliseconds, microseconds, or nanoseconds) with appropriate changes in circuit parameters.

Homeostatic Component

The homeostatic component, S, can be understood in terms of sleep pressure or need for sleep. From the time a person wakes up, the sleep pressure begins to rise and continues to rise until the beginning of the next sleep episode. The sleep pressure decays from the beginning of the sleep episode, i.e. the need for sleep starts reducing. Hence during wake time, there is an exponential rise in sleep pressure, and during sleep there is an exponential decay in sleep pressure. Alertness can be estimated by modeling the inverse of the homeostatic component, 1-S.

Figure 4A:
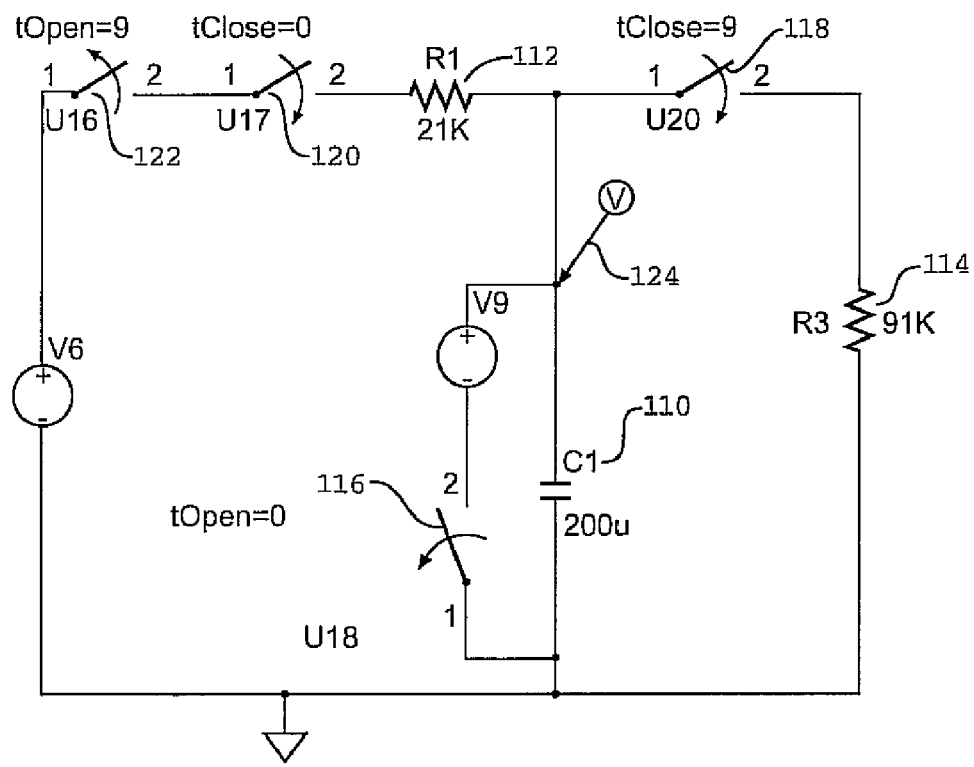
FIG. 4A illustrates a first analog circuit, a switched RC circuit, for modeling the homeostatic component of alertness.

FIG. 4A shows an analog circuit that can be used to model the homeostatic component S, in this particular example by modeling the inverse 1-S. This analog circuit includes a capacitor 110, a first (charging) resistor 112 and a second (discharge) resistor 114. The circuit includes a plurality of switches, such as switch 118 which may be opened and closed in relation to sleep-wake transitions. At a time t=0 (start of first sleep period) the switch at 120 is closed, and the switch at 116 is opened. At this time the capacitor 110 charges from the source V6 through the charging resistor shown at 112. At time t=9 (seconds, with temporal scaling) the switch at 122 is opened (start of waking period) and the switch at 118 is closed. The capacitor now discharges through the discharge resistor indicated at 114. This alternating switching process can be repeated at the appropriate times to represent collected sleep and wake times. Sleep and wake times can be recorded over periods extending beyond a single day, to allow rapid simulation of the effects of a person's extended sleep-wake patterns, and to contribute this homeostatic alertness component to the estimated alertness. For the homeostatic component, as well as for the other components, the modeled sleep wake cycle may cover a plurality of days, and not just the most recent sleep-wake period.

Figure 4B:
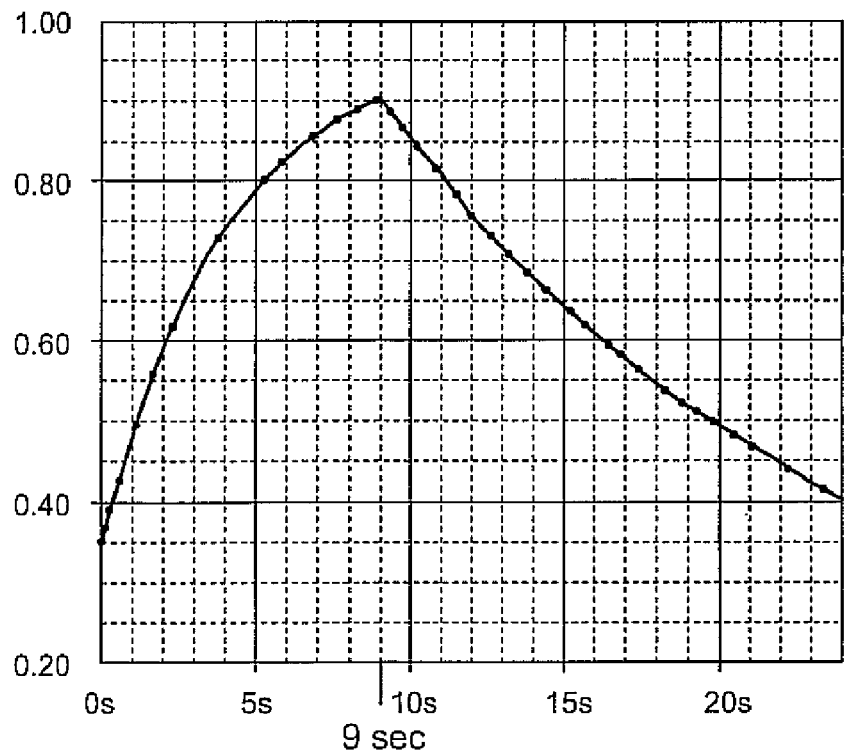
FIG. 4B illustrates a typical output from the circuit of FIG. 4A.

FIG. 4B is a graph showing the charge and discharge of the capacitor, in terms of the voltage obtained at point 124 in the circuit. This graph was obtained using a circuit model (PSPICE, Cadence, San Jose, Calif.). The charge and discharge of the capacitor through resistances can be used to model the homeostatic component of the sleep-wake cycle. The circuit is striking in its simplicity, allowing a miniaturized device to be made. FIG. 4B shows the charging from time 0 to 9 seconds (here, temporal scaling is used so that each second of the simulation represents one hour of the actual sleep-wake cycle), and discharge after the time 9 seconds. In this particular example the time scale is in seconds, however in a practical device the charging and discharging can be adjusted using appropriate choices of resistors and capacitors to provide realistic representations of human alertness changes.

In FIG. 4B, the rate of increase in 1-S is initially high, and the rate of increase within the sleep state falls as time progresses. Hence, a short sleep can be highly beneficial. In this example, the simulation is run over a time scale of 1 second representing 1 hour. However, the simulation could also be run over other time periods, in particular shorter time periods (such as over milliseconds, microseconds, or nanoseconds) with appropriate changes in circuit parameters.

The homeostatic component (in this example the inverse 1-S) is modeled using the voltage across the capacitor while it is charging and discharging in the RC circuit. The charging portion on the left of FIG. 4B represents sleep, and the discharge represents a waking state. In this example, the decay time constant is 4.2 sec, and the rise time constant is 18.2 sec. The capacitor charges and discharges through different resistors. Resistors may be voltage-controlled resistors, such as field effect transistors, allowing for tuning of charging and discharging time constants, so as to allow adjustment of the model. The time of charging and discharging the capacitor, related to sleep-wake transitions, may be selected using a voltage-controlled switch. In some examples, a capacitor may be charged and discharged through the same adjustable resistor, the adjustable resistor having a first resistance for charging and second resistance for discharging.

The inverse 1-S may also be understood as follows. When the person is asleep, a reservoir of energy fills up. While when the person is awake, the reservoir is depleted. The waveform of FIG. 4B shows an exponential rise (reservoir filling) when the person is asleep and an exponential decays (reservoir depletion) when the person is awake.

The recovery process, or rise rate of 1-S during sleep, can further depend upon the length of the prior awake time. For example, if a person has been awake for a long period of time, adenosine levels in the blood are typically high. During a following sleep period, even for a short sleep period, the recovery (corresponding to a drop in adenosine level in a biochemical model) may be faster.

In an analog circuit model, this can further be represented by a faster charge rate of a capacitor. This may be achieved by adjusting the value of the charging resistor. For faster capacitor charging, the corresponding resistor value is decreased. This may be achieved using an adjustable resistor, such as a voltage-controlled resistor, for example a FET (field effect transistor). Effectively, a circuit model may represent an estimated adenosine level as a voltage value to control a voltage-controlled resistor, which in turn controls the charging and/or discharging of the capacitor. The capacitor may be a voltage-controlled capacitor.

This approach allows estimation of the optimal time and duration of the sleep period (such as a nap) to get the best recovery sleep. For different levels of adenosine, the recovery rate can be modeled using an analog electrical system. Adenosine levels can be mapped to a voltage level that will control the voltage controlled resistor (FET), for example using a voltage derived from the charge on the capacitor.

Inertial Component

The inertial component is activated at a sleep-wake transition, and is present in two forms. Sleep inertia occurs after the transition from sleep to wake, and wake inertia occurs at the transition from wake to sleep. Sleep inertia describes a feeling of grogginess most people experience after awakening. Sleep inertia can last from 1 minute to 4 hours, but typically lasts 15-30 minutes. During this period, a person is at a reduced level of alertness and may have trouble doing even simple tasks. Wake inertia describes the difficulty in falling asleep.

Figure 5A:
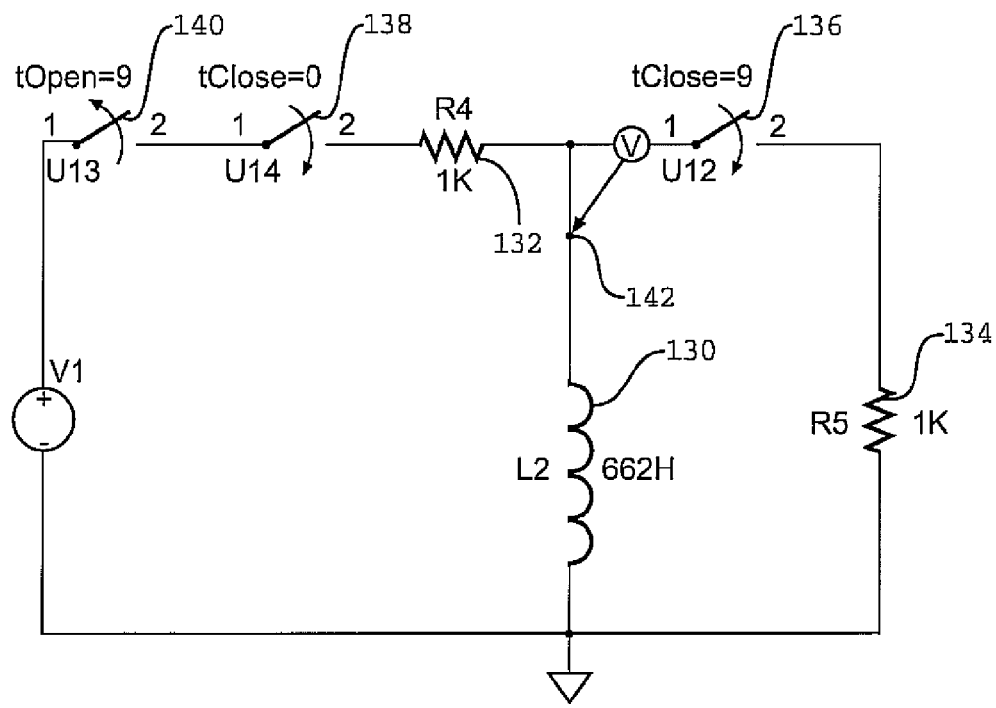
FIG. 5A shows a second analog circuit, a switched RL circuit, for simulation of the inertial component.

FIG. 5A shows a second analog circuit that may be used for modeling of the inertial component of the sleep-wake cycle. The circuit comprises inductor 130, first resistor indicated at 132 and second resistor indicated at 134. At the time T=0 the initially open switch at 138 is closed and the voltage at circuit point 142 undergoes a transient response with a sharp rise and then approximately exponential fall. At a later time initially closed switch 140 is opened and the initially open switch 136 is closed at which time energy stored within the magnetic field of the inductor is discharged through the resistor at 134. A negative polarity transient is then observed at circuit point 142.

In this example, the inertial component is modeled by the voltage across the inductor during switching transients, when energy stored in the inductor is dissipated through the discharge resistor. Resistors may be voltage-controlled resistors, such as field effect transistors, allowing for model tuning. Switching times, corresponding to sleep-wake transitions, can be implemented using voltage controlled switches.

Figure 5B:
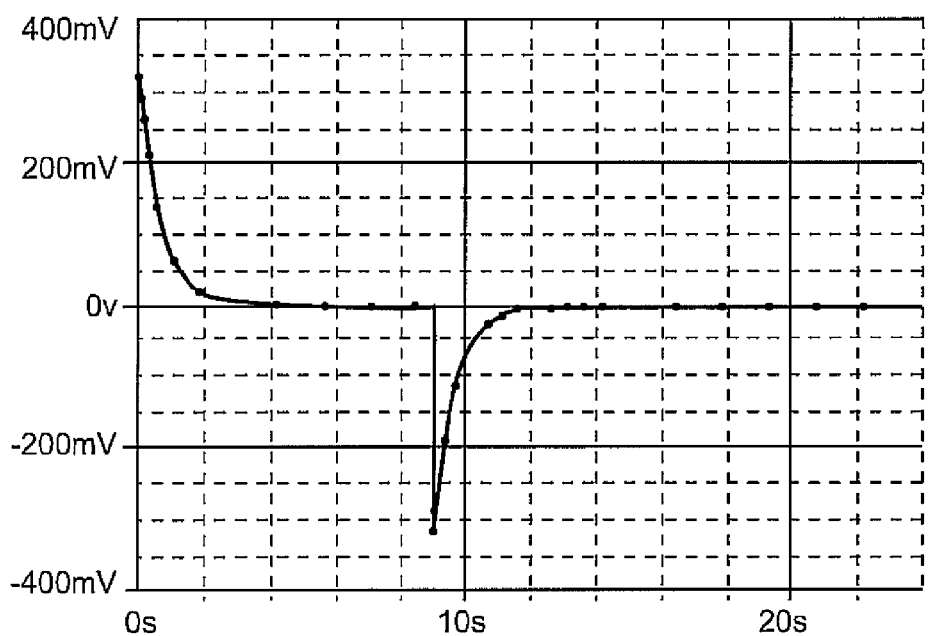
FIG. 5B shows a typical output from the circuit of FIG. 5A.

FIG. 5B shows the voltage at circuit point 142 as a function of time, obtained using a circuit model. The transients at 0 and 9 seconds correspond to the opening and closing of switches discussed above. These transients, and also the transition to charge and discharge of capacitor in FIG. 4B are related to the sleep-wake transitions for the individual. For example after waking the inertial component reduces alertness for a relatively short time period as indicated by the spike decays in FIG. 5B. In this example, temporal scaling is used in which one second of simulation time represents one hour of the modeled sleep-wake cycle. In this case, a temporal scaling parameter of 3,600 is used, reducing the simulation time by a division factor of 3,600 relative to a real time simulation. In other examples, the temporal scaling parameter may be other values, for example greater than 1,000, in some examples greater than 1 million, and in some examples greater than 1 billion. The simulation could also be run over other time periods, in particular shorter time periods (such as over milliseconds, microseconds, or nanoseconds) with appropriate changes in circuit parameters.

Figure 6:
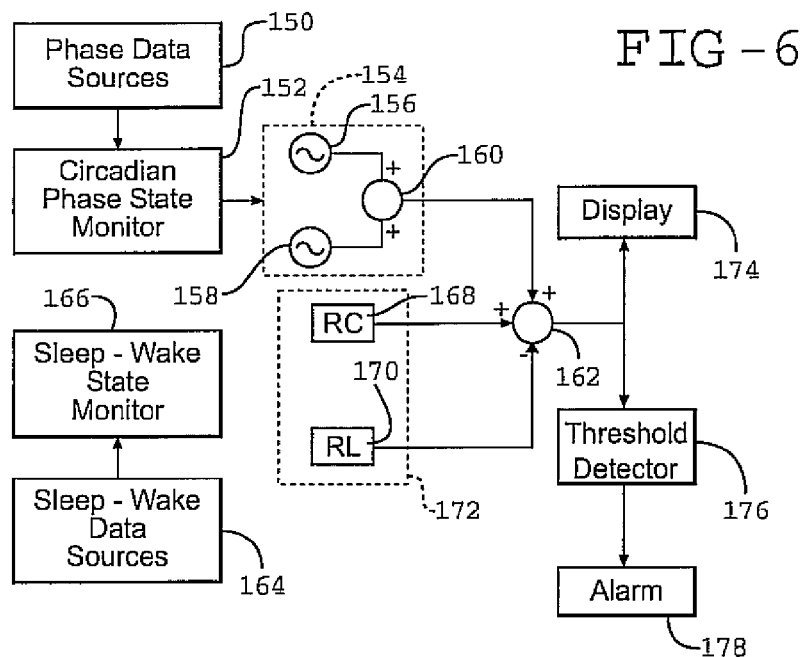
FIG. 6 is a simplified schematic showing an electronic circuit receiving data from sleep-wake data sources and circadian phase data sources.

FIG. 6 is a further schematic of an alertness monitor according to an example of the present invention. The circadian model is indicated at 154, including first and second amplifiers 156 and 158 and summation at 160. The circuit shows phase data sources 150 providing phase data to a circadian phase state monitor at 152. Phase data sources may include data from light sensors that monitor the light levels experienced by the person. For example if a person changes time zone, the pattern of light and darkness will change and this can be detected by the circadian phase state monitor and used to adjust the phases of the oscillators within the circadian model. The figure also shows sleep-wake data sources at 164 that provide sleep-wake data to a sleep-wake state monitor at 166.

The outputs from the model circuits, representing circadian, homeostatic and inertial components, are then combined using a non-inverting summing amplifier. The output of the summing amplifier can be used to represent the alertness of the person.

The transitions from waking to sleeping state are passed to switches within the first and second analog circuits 168 and 170. The box 172 indicates generally the tunable analog circuitry within the electronic circuit. The outputs from the circadian component model 154 and the analog circuit outputs from the analog circuitry at 172 are combined at the summing amplifier 162 and used to provide display information at 174.

A threshold detector 176 may be used to determine if the alertness has fallen below one or more threshold levels, allowing an alarm 178 to be sounded or otherwise given to the person. A first threshold may lead to a relatively gentle alarm, and a second threshold for example being very close to a sleeping state may lead to a more vigorous alarm being given.

Sleep-wake data sources may include any source of information regarding the sleep or waking state of the person. For example this may include outputs from activity sensors, such as accelerometers. A position sensor such as a GPS may be used to determine location, and the position data, along with any other available data such as ambient lighting, activity level, or other data, can be used to determine if the person is asleep or awake. Additional information about the state of the person may be further inferred from the position data, or combinations of the position data with other data. The sleep-wake state monitor detects changes in the sleep-wake state, as determined from the sleep-wake data.

Figure 7:
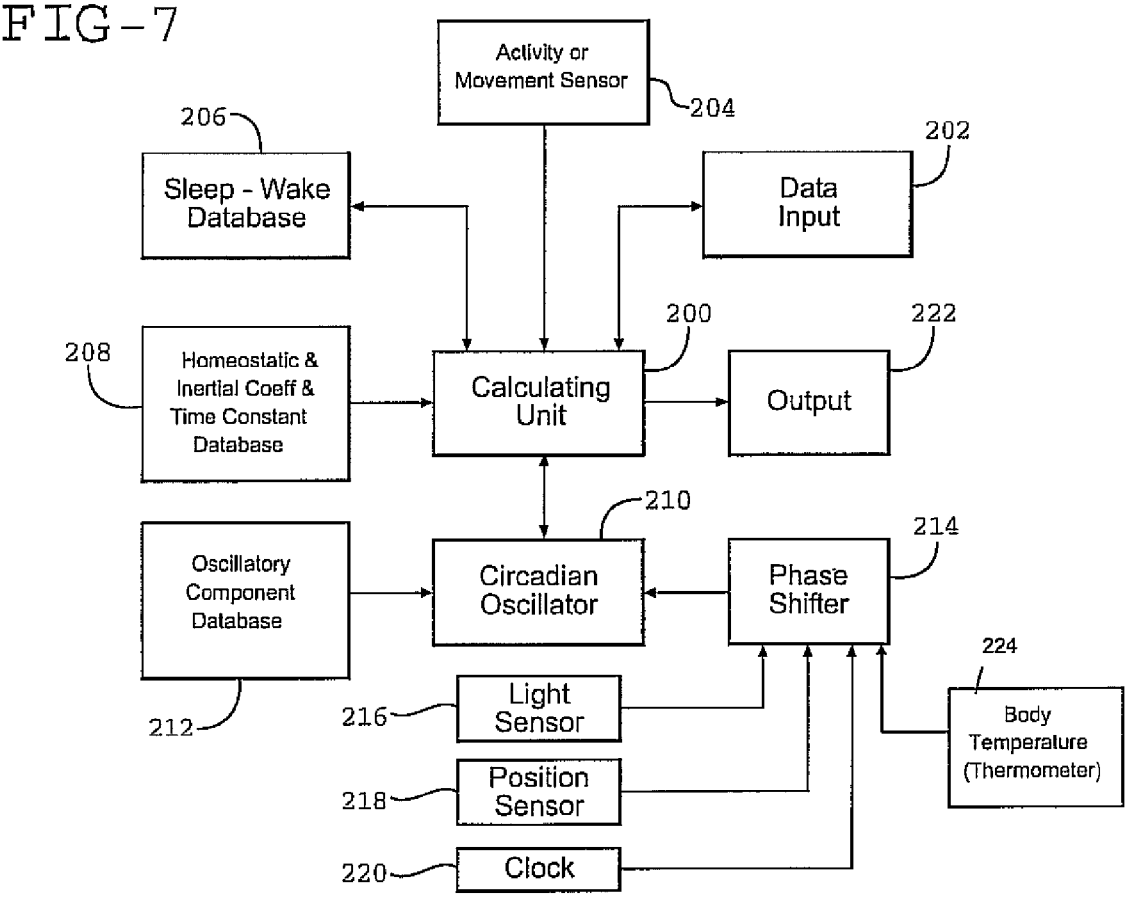
FIG. 7 is a further schematic of an example apparatus, illustrating details of the inputs and data sources used in operation.

FIG. 7 is a further schematic of a circuit useful for an alertness monitor. This schematic includes a calculating unit 200 receiving data from a data input 202, activity data from an activity sensor 204 (such as an accelerometer or other sensor providing a signal correlated with activity or movement of the living subject), sleep-wake transition data from memory, in this case a sleep-wake database 206, and further modeling parameters from a homeostatic and inertial coefficient and time constant database 208. The circadian component model, including oscillator circuits, at 210 receives data from a circadian oscillatory component database 212. The circadian oscillatory component database may include, for example, times at which the circadian oscillations peak, both for the 12-hour and 24-hour oscillatory components. Additional circadian oscillatory components may be included, for example 8 hour components, approximately 28 day (lunar cycle) components, and 365 day (solar cycle) components. The phase shifter 214 is used to modify the phases of one or both of the circadian oscillators. The phase shifter circuit receives data from a light sensor 216, a position sensor 218, a clock 220, and a thermometer or other body temperature sensor 224. In other examples, the phase shifter may also receive signals from the activity or movement sensor 204. For example, the position sensor may be a GPS unit, allowing phase shift data to be provided to the circadian component model oscillators upon change in time zone. An estimated alertness is received at the output 222. The data input 202 may receive data from one or more sensors, and also from local and wide area communication networks. Received data may include local time, position, sunset and sunrise time, and the like.

The homeostatic and inertial coefficient and time constant database may be used to store analog circuit parameters for use in the homeostatic or inertial modeling within the calculating unit. These may be adjusted by user input. In some cases, a data input or other user input can be used to compare the predicted alertness from the output of the circuit 222 with the actual state of the modeled person.

Further, the output may be compared with the data obtained from a physical activity sensor. The activity sensor may be an accelerometer, pedometer, or other device that provides a sensor output correlated with physical activity (and/or movement) of the person. An activity sensor may also be a pulse rate sensor, if the person's pulse rate is correlated with physical activity.

Figure 8:
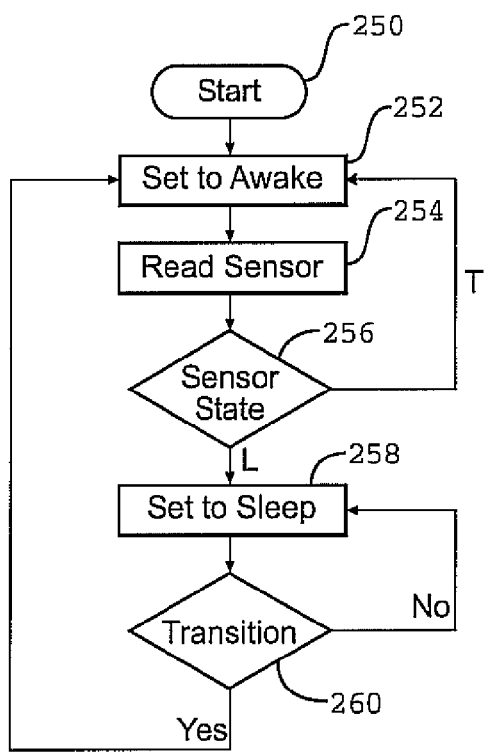
FIG. 8 is a flowchart showing detection of sleep-wake transitions using a sensor.

FIG. 8 is a flowchart of a method for determining transition states within the sleep-wake cycle. After the start 250, the sleep-wake state is set to awake at 252. The sensor, for example an activity sensor, is read at 254, and the sensor state determined at 256. If the sensor state indicates that the person is physically active (T), the state is set to awake at 252. However if the sensor state indicates a low level activity (L), the sleep-wake state is set to sleep at 258. Detection (at 260) of a further sleep-wake transition results in a transition back from sleep to awake via Set to Awake 252. Thus the state to changes cyclically when a transition is detected from awake to sleep at 256 or from sleep back to wakefulness at 260. In between these transitions, the system maintains an indication of the current state of sleep or wakefulness.

Figure 9:
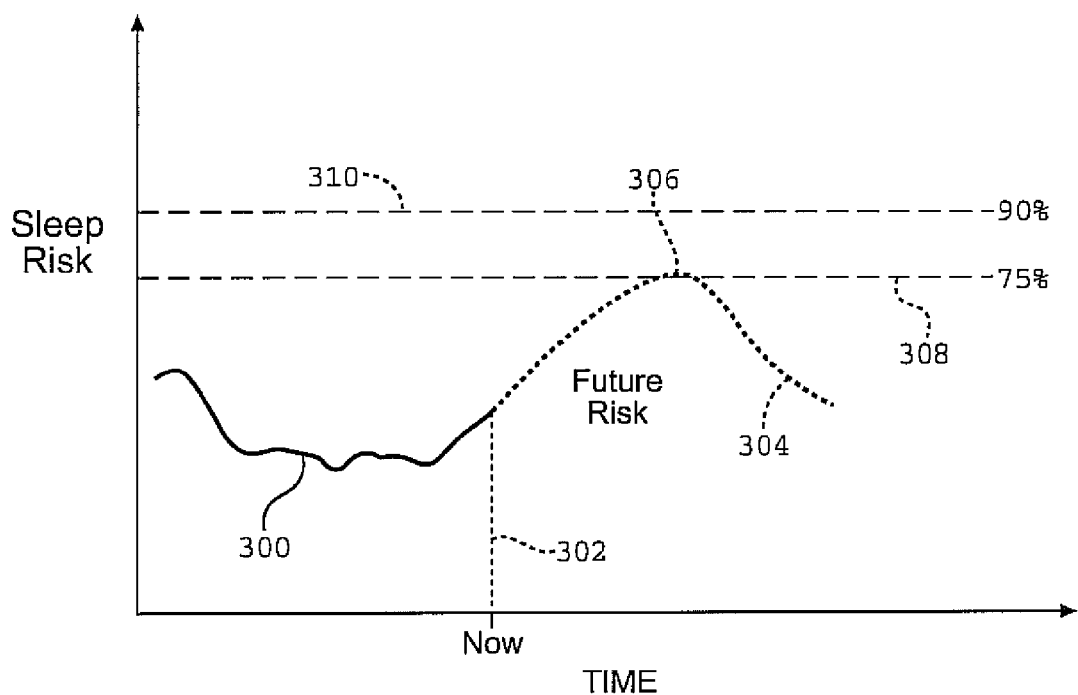
FIG. 9 represents a possible output of an alertness estimator.
Figure 15:
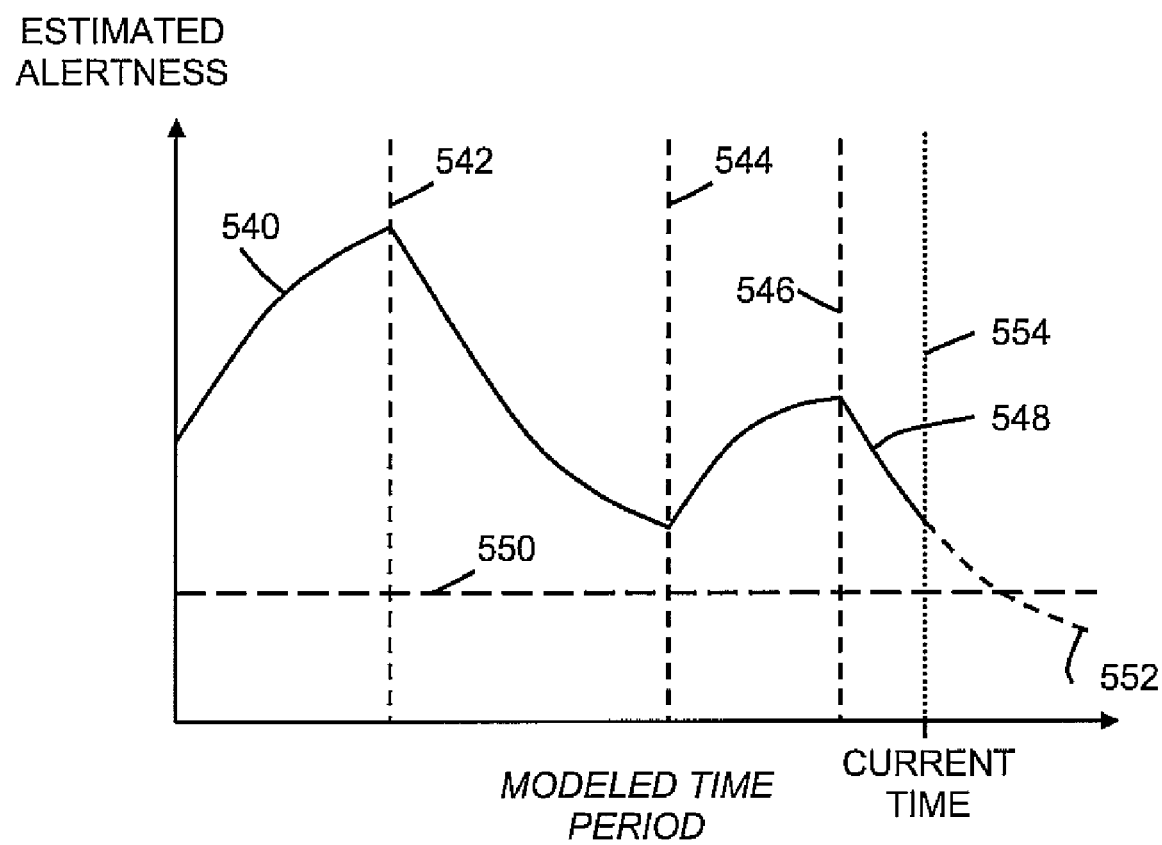
FIG. 15 illustrates estimation of current and/or future alertness.

FIG. 9 shows a possible estimated alertness output at 300 as a function of time. The current time is indicated on the axis at 302. The sleep risk may be calculated in terms of the alertness level, a low alertness level corresponding to a high sleep risk. In some examples of the present invention, the display may show future predicted alertness levels. In this case the future predicted alertness 304 is shown as a dashed line and crosses a predetermined threshold at 306. Hence, a person can plan their future activities so that they are not engaging in difficult or dangerous tasks at times at which the sleep risk is excessive. A second threshold at a higher sleep risk is also shown. A different or more prolonged alarm may be given if the sleep risk exceeds the higher threshold. The two thresholds are shown at dashed lines 308 and 310 respectively. In this example, sleep risk is shown which increases as estimated alertness falls. In other examples, estimated alertness may be presented, for example as shown in FIG. 15.

Figure 10:
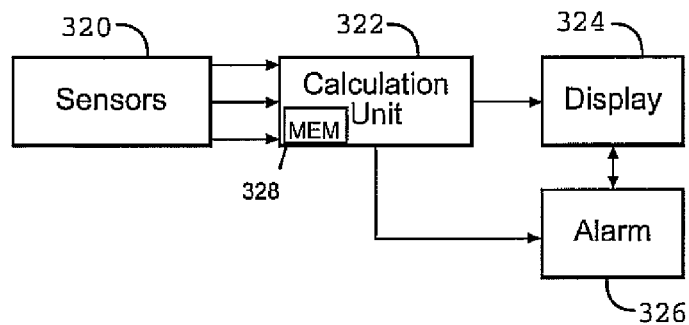
FIG. 10 shows a highly simplified schematic of a further example alertness estimator.

FIG. 10 shows a highly simplified schematic of an alertness estimator. The alertness estimator comprises one or more sensors at 320 providing sensor data to a calculation unit at 322. The calculation unit may include an electronic circuit for modeling discussed elsewhere, as well as a memory unit 328 to facilitate time-scaled operation of the system. A memory unit may also support one or more databases such as a circadian oscillatory component database, a homeostatic and inertial coefficient and time constant database, and possibly other databases. The calculation unit provides alertness levels to a display 324 and an alarm 326. The display may allow the user to see a graphical display of previous, present and future alertness levels against predetermined thresholds. The display may also be used to show planned activities and give warnings if activities are planned at times of low alertness. The alarm 326 may be used to warn a person if a dangerous situation is detected, for example if the person is at a low alertness level.

Figure 11:
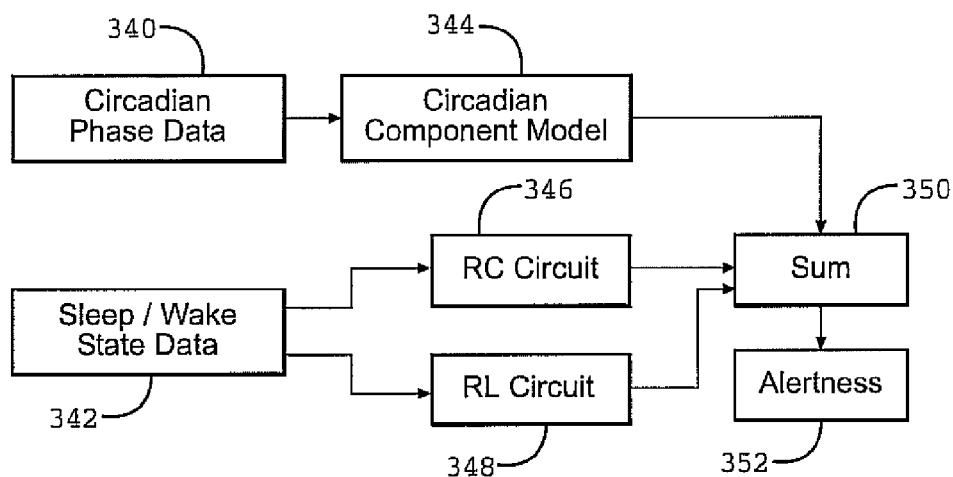
FIG. 11 shows a further highly simplified schematic of an alertness estimator.

FIG. 11 is another simplified schematic showing circadian phase data 340 provided to circadian component model 344, sleep-wake state data 342 being provided to RC circuit 346 and RL circuit 348 and a summing circuit 350 providing the alertness level at 352. The circadian component model may be an electronic circuit operable to model circadian components of the sleep-wake cycle, and may include multiple electronic circuits.

Figure 12:
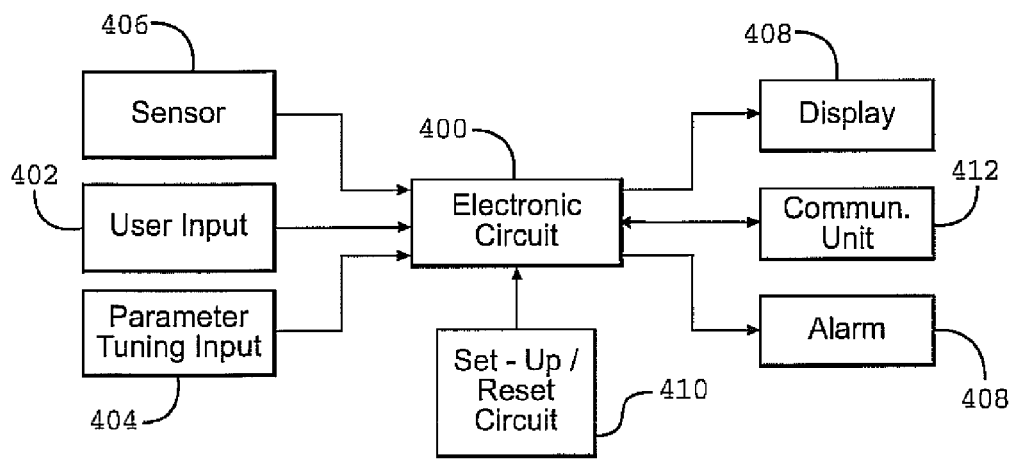
FIG. 12 also shows a simplified schematic of an example of the present invention.

FIG. 12 is a schematic representation of another example. In this example, the alertness monitor includes an electronic circuit 400 including modeling electronic circuitry such as described herein, a user input 402, a parameter tuning input 404, a sensor 406, an alertness display 408, a communications unit 412, and a setup and reset circuit 410.

The parameter tuning input allows adjustment of RC and (optionally) RL parameters. For example, voltage-tunable resistors may be adjusted. In some cases, adjustable resistors may be adjusted mechanically.

The communications unit allows transmission of alertness data to a remote location, and can be used for remote monitoring of a person.

Figure 13:
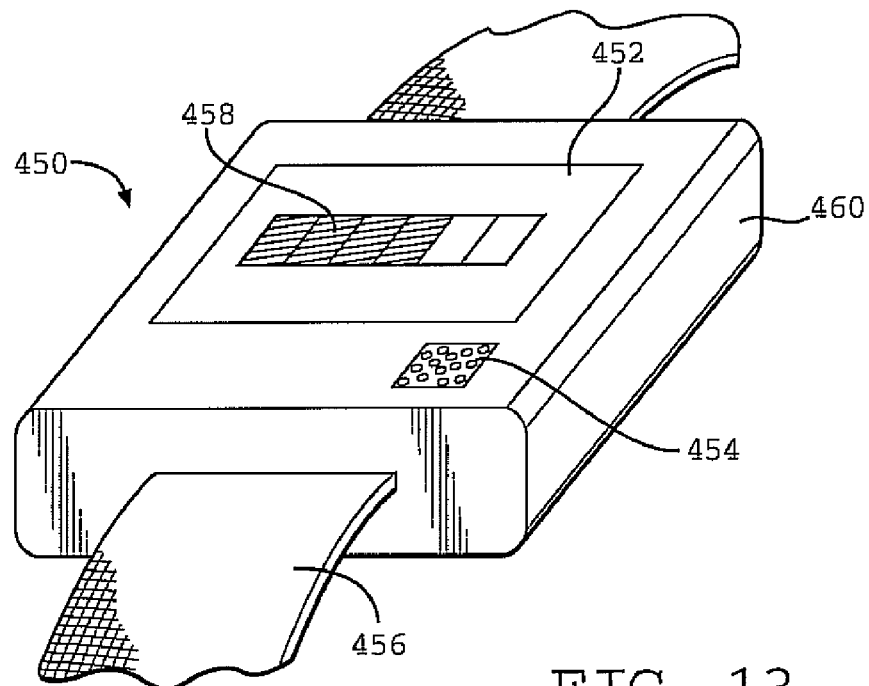
FIG. 13 shows a wrist-mounted embodiment.

FIG. 13 shows another possible embodiment, a wrist-mounted device 450 comprising housing 460, display 452 (showing bargraph 458), audible alarm output 454, and strap 456. In this embodiment the housing 460 has an attached strap configured for strapping around a portion of the person's anatomy, in this example the wrist. However, in other examples, a device may be strapped to an ankle, around the chest, or otherwise located.

For example, a wrist-mounted device may be provided including an electronic circuit as described elsewhere in the specification, and further including an accelerometer and/or pulse rate monitor. Using the outputs from an accelerometer and/or a pulse rate monitors, the sleep-wake state of the person may be determined, and the modeling capability of the electronic circuit (not shown in this figure) used to generate a display of alertness level on the display 452 and provide audible warnings to the audible alarm (e.g. a buzzer) 454 if desired.

Embodiments of the present invention can be combined with other functionalities. For example the wrist-mounted device shown in FIG. 13 may be combined with the functionality of a wristwatch, personal communication device, music player, pulse rate monitor, fitness monitor, or any other function desired.

In some examples, intake of a stimulant such as caffeine may be accounted for through, for example, addition of charge to a capacitor in a tuned circuit, or similar approach.

Sleep-Wake Transitions

The term "sleep-wake transitions" is used to refer to transitions between the sleeping state and the waking state in either direction, i.e. transitions from waking to sleeping or vice versa.

Figure 14:
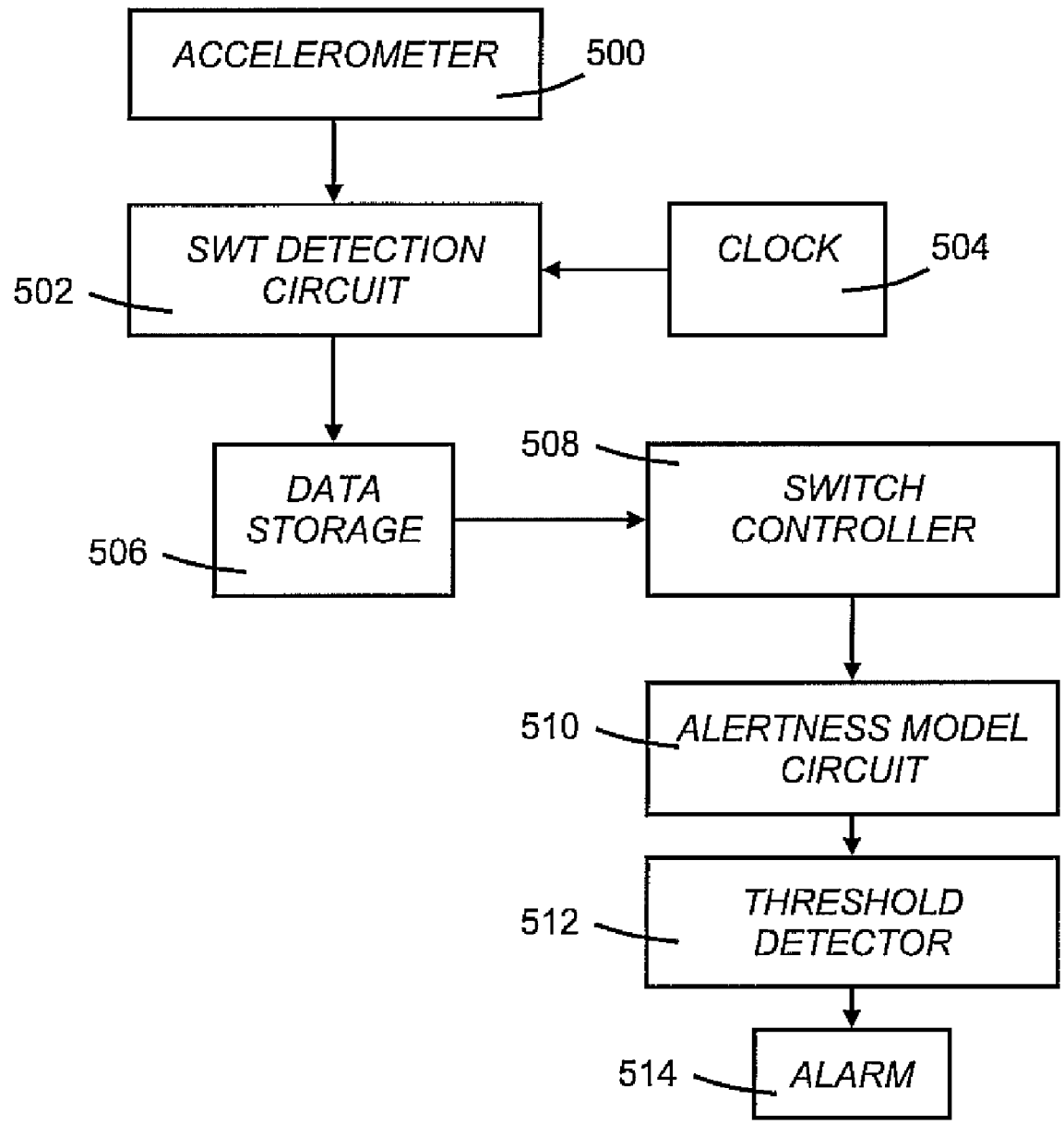
FIG. 14 shows a circuit including a sleep-wake transition detection circuit.

FIG. 14 shows a circuit comprising an activity sensor (in this example, accelerometer 500), sleep-wake transition detection circuit 502, clock 504, data storage 506, switch controller 508, alertness model circuit 510, threshold detector 512, and alarm 514.

In this example, an activity signal from the activity sensor is received by the sleep-wake detection circuit. Transitions to and from the sleeping state (generally termed sleep-wake transitions) are detected from the change in time dependence of person's activity, as monitored by the activity sensor. For example, a decrease in time-averaged signal amplitude (for example, averaged over one or more minutes) may be used as an indication of a sleep-wake transition.

The data storage 506 (for example, a memory chip) is used to store sleep-wake transition times. In some examples, such times may be entered into an apparatus using an input mechanism and stored in memory.

The switch controller circuit is used to actuate (or toggle) one or more switches in the alertness model circuit in response to stored sleep-wake transition times. In some examples, for real time operation (temporal scaling parameter=1), the data storage can be omitted and the switch controller is responsive to detected sleep-wake transitions in real time.

Temporal Scaling

In some examples of the present invention, temporal scaling is used to estimate alertness. An electronic circuit simulates alertness over a simulated time period, which may include future time periods, the electronic circuit performing the simulation over a much shorter time scale than the simulated time period. For example, alertness estimates for one or more hours, or one or more days, may be estimated in a matter of seconds (or milliseconds), depending upon the temporal scaling factor used. Temporal scaling facilitates future alertness estimation, and provides an improved method of personal planning, such as event or task scheduling. Temporal scaling can also be used to estimate a present alertness using stored sleep-wake transition time data.

In temporal scaling, circuit operation time is less than the modeled time period for a person, by a factor which may be termed the temporal scaling parameter. In examples discussed above, one second of model circuit operation was used to represent one hour for the person, corresponding to a temporal scaling parameter of 3600. However, these examples are illustrative and are not intended to limit the invention. In some examples, the temporal scaling parameter may be greater than 1000, in some examples greater than 1 million, and in some examples greater than 1 billion.

FIG. 15 shows an alertness estimate (curve 540) as a function of time. In this example, dashed lines 542, 544, and 546 represent sleep-wake transitions, lines 542 and 546 representing awakening times and line 544 representing a time at which the person goes to sleep. The current time is represented by dotted line 554. Using temporal scaling, and for example sleep-wake transition times stored in a memory such as described above in relation to FIG. 14, a circuit can estimate alertness up to the current time (line 540, including most recent segment 548), and further during future times as a projected estimated alertness shown in the Figure as curved dashed line 552. In this example, the projected estimated alertness falls below a threshold alertness 550, so that an alarm is given to the person.

In this example, the inertial component is neglected. An alarm may be given if a person attempts to plan an event less than an inertial recovery time after awakening. An inertial recovery time corresponds to a time period over which the inertial component would decay to a negligible level, for example one hour. The inertial recovery time may be adjustable by a person using the apparatus. The apparatus may display a time remaining before alertness is predicted to fall below a threshold level.

Microsecond or nanosecond time scales can be used to represent a simulated time period, with appropriate selection of component values. The simulated time period may represent one or more days, one or more work shifts, or in some cases may be used to determine alertness over longer periods. For example, a month long time period may be simulated to investigate the likely effect of work shift, sleep time, and/or time zone changes. The simulated time period may include previous and/or future times. An apparatus may include a data entry mechanism, such as a keypad, allowing them to enter planned future information, such as sleeping times, work times, and the like, to investigate if a planned schedule presents alertness issues that may present safety or other issues.

Temporal scaling can be used so that the sleep-wake cycle and alertness can be simulated using the electronic circuit at very fast time-scale. The term temporal scaling refers to simulations using time-scales significantly shorter than the actual simulated time periods. Proportionality can be retained using a temporal scaling parameter. For example, a temporal scaling parameter of 3,600 may be used, representing one second per hour. In other examples, one second or less of simulation time can be used per simulated hour. In some cases, a simulation may use 1 millisecond or less, or 1 nanosecond or less, per simulated hour.

For example, the charging or discharging time of a capacitor may be reduced by the appropriate scaling parameter, for example using a lower value of charging resistance and/or a lower value of capacitance. One or more switches may be operable to change the operational mode of the apparatus between real time mode and temporal scaling mode.

Phase Shift Circuit

Example apparatus include an electronic circuit comprising a circadian component model circuit having an associated phase shift adjustment circuit operable to modify relative phases of the first component and the second component (and/or other components, if these are present). In some examples, a light sensor provides a light sensor signal to the phase shift adjustment circuit, the relative phases of the first component and the second component being adjustable in response to the light sensor signal. The effect of light exposure on circadian rhythms may be implemented, for example by applying phase delays and/or phase advancement to the components as a function of light intensity, duration of exposure, integrated total exposure, and/or time (relative to the sleep-wake cycle) of exposure. For example, an electronic circuit may model the circadian component as inducing sleep at a particular time, conventionally at night. A light exposure during this time, for example due to time zone change, may be used to add phase delays or advances to one or both components.

A position sensor can be used to provide a position signal, and this may be used to calculate a local time zone, the phase shift adjustment circuit receiving the position signal (or, equivalently, a local time signal), the relative phases of the first component and the second component being adjustable in response to position signal.

The oscillatory output of the circadian model circuit may include a third component, and in some cases further components. The amplitude and relative phase of the third component may be adjustable so as to improve accuracy of the circadian model circuit.

Applications

Embodiments of the present invention include improved methods to determine whether it is safe to do manufacturing work (such as for shift workers), to operate heavy equipment or machinery (such as for long-haul truckers, airline pilots, heavy equipment operators, or others), or to make critical or time-critical decisions such as in medicine, nuclear control operations, aerospace applications, or other safety-critical applications. For example, a method may include estimating a current alertness for a person, and providing a warning if the person's alertness is less than a predetermined threshold. Examples may also include estimating alertness for a range of future times, for example between a start time and an end time, and providing a warning if the estimated alertness falls below a predetermined threshold within that time. The start time may be a current time or a future time, and the start and end times may correspond to start and end time of a work shift, event, or other time period for which a person desires to be alert.

Embodiments of the present invention may improve safety. For example a person may be provided with an alertness monitor according to an embodiment of the present invention. The alertness monitor may communicate with other electronic circuitry, including monitoring systems, environmental controls, computing devices, and the like, and a visual and/or acoustic alarm to the person may be provided if a person's present or predicted near-future (e.g. next hour) alertness level falls below a predetermined threshold. Equipment may be disabled (possibly after a prior warning), an entertainment system may be turned on or reconfigured to provide stimulating output, ambient temperature lowered, air circulation increased, or other modification to the environment provided if the person's alertness level falls below a predetermined threshold.

Living Beings

Examples of the present invention relate generally to apparatus and methods for the estimation of alertness of a living being. Examples discussed elsewhere relate to a person's alertness, but the invention is not limited to humans, and examples can be used to estimate the alertness of any living being having sleep cycle components such as those discussed herein, including other mammals. For animal (non-human) applications, a system may include one or more sensors configured to be supported by the animal and a display and computation unit adapted to be carried or supported by a person. A computation unit may receive sensor data from the sensors using a wireless or other connection.

For example, the alertness of a racing animal, such as a horse or dog, may be estimated for the time of a race or show (which may be a current or future time) using example apparatus and methods according to the present invention.

Adjustable Devices and Tunability

System set-up and tuning information can be provided to allow user customization of the device and initialization and re-initialization. An apparatus may further include a data port, light sensor, a memory (for example to store determined sleep-wake or wake sleep transition times), allowing rapid analog simulations, re-simulation (for example, after tuning the apparatus), and prediction. The apparatus can be used to give a simulation of future alertness up until a future time, using previous (and in some cases, planned) sleep-wake transitions.

An apparatus may be configured with one or more analog circuits having tunable time constants. Time constants may be tuned to improve simulation accuracy, or in some cases to modify the scaling parameter (for example if simulating a longer time period). One or more components in an analog circuit may be adjustable, for example one or more voltage-tunable capacitors and/or resistors may be used in a tunable RC circuit.

An apparatus may be configured with tuning controls, by which the circuits used to model the homeostatic, inertial, and/or circadian components may be adjusted. For example, tuning controls may comprise potentiometers or other adjustable electronic devices accessible to a user, for example mounted on a housing of the apparatus. Initial settings may correspond to average values. Average values may be determined or estimated across an entire population, or be for a specific gender, age, or other demographic group. A person may monitor sleep-wake transitions and periods of seemingly high or low alertness during a training period, with deviations from the modeled alertness used to adjust variable component values (such as one or more resistance, capacitance, and/or inductance, as appropriate) in the circuits used. For example, a person may require a longer than average time period to gain high alertness in the morning, so that the time constants of the inertial model circuit may be correspondingly adjusted.

Display of Alertness Estimate

An alertness estimate may be calculated as a numerical parameter, for example between a minimum value and a maximum value. The minimum value may be set to be zero. The maximum value may correspond to the maximum voltage available from a model circuit, for example close to the supply voltage. For display to a person, the alertness may be presented as a numerical parameter between a minimum value (e.g. 0) and a maximum value (arbitrary, for example 1, 10, or 100), and may be expressed as a percentage of a maximum or other reference level. A bargraph may be used, e.g. with green LED bars for higher alertness estimates and red bars for lower estimates. Other approaches to visual display of alertness may be used. In some cases, an electronic display such as an LCD can be used, for example to display an alertness estimate as a function of time.

Other Aspects

An example method of determining alertness includes modeling the circadian component of the sleep-wake cycle using a function generator, modeling the homeostatic component using a first analog circuit, modeling the inertial component using a second analog circuit, and combining the outputs thereof so as to estimate alertness.

Examples of the present invention include an apparatus which is configured to use a person's recent sleep and waking history to estimate their alertness, and provide feedback to the person, facilitating task selection. A tunable analog electrical circuit can be used to estimate human alertness, and feedback to a person allows the person to modify their behavior or task selections accordingly. Alertness information can increase human safety, task performance, and efficiency. Factors that influence human alertness can be modeled to estimate a current alertness, given a recent history of sleep and waking states. Alertness levels can be displayed continuously to a person, and alarms can be programmed to warn the person, or another person, when alertness is falling below a threshold.

The use of analog electrical circuit elements allows examples of the present invention to be smaller, lighter, and more portable than conventional approaches. The use of specifically tailored analog circuits can permit faster execution of an alertness model, compared with conventional initialization and running time of a digital computer. An analog system may also have less weight and less energy usage compared to use of a general computer operating system and software environment. Further, the described alertness model provides information relevant to near-term (for example, within a current wake cycle) safety-related task engagement or disengagement decisions.

An example apparatus may include one or more inputs, an electronic circuit operable to provide an estimate of alertness, a visual representation of alertness such as a display, an optional alarm, and an optional parameter tuning mechanism. For example, resistor values (and in some cases, capacitor and/or inductor values) may be adjusted to improve model representation. Input data may include light/dark cycle of the local environment, and sensor data representative of a recent history of sleep wake times and a current state of sleep or wakefulness.

In other example circuits, a digital representation of an analog circuit may be used. For example, an apparatus according to an embodiment of the present invention may be a portable computing device, such as a personal organizer, cell-phone, portable computer, or some combination of such devices. The portable computing device may include a processor, and may execute software so as to simulate the functionality of an analog circuit. Such circuit simulation software is known in the electronic art, and need not be described in more detail here.

Hence, an apparatus may include a processor capable of executing software representative of one or more analog circuits, such as a resistor-capacitor analog circuit so as to simulate the homeostatic component, and optionally a resistor-inductor analog circuit so as to simulate the inertial component. The apparatus may have other functionalities, such as an organizer, computer, phone, and the like.

Examples of the present invention include a lightweight tunable analog circuit operable to model human alertness and configured to drive display and warning feedback mechanisms. Alertness information can be taken into account during an improved decision malting process, allowing better task selection, performance and safety.

The invention is not restricted to the illustrative examples described above. Examples described are exemplary, and are not intended to limit the scope of the invention. Changes therein, other combinations of elements, and other uses will occur to those skilled in the art. The scope of the invention is defined by the scope of the claims.

Having described our invention, we claim:

1. An apparatus for estimating alertness for a living being having a sleep-wake cycle, the sleep-wake cycle having at least a circadian component and a homeostatic component, the apparatus comprising:
    an electronic circuit, including:
        a circadian model circuit configured to model the circadian component, and
        a homeostatic model circuit configured to model the homeostatic component of the sleep-wake cycle,
    the homeostatic model circuit including a resistor-capacitor analog circuit,
    the electronic circuit being operable to combine outputs from the homeostatic model circuit and the circadian model circuit so as to estimate the alertness.

2. The apparatus of claim 1, wherein the electronic circuit further includes an inertial model circuit configured to model an inertial component of the sleep-wake cycle,
    the inertial model circuit including a resistor-inductor analog circuit,
    the electronic circuit being operable to combine outputs from the homeostatic model circuit, the inertial model circuit, and the circadian model circuit so as to estimate the alertness.

3. The apparatus of claim 1, the resistor-capacitor analog circuit including a capacitive element, a first resistive load, and a second resistive load,
    the capacitive element being charged through the first resistive load and discharged through the second resistive load,
    the homeostatic component being modeled using a potential difference across the capacitive element,
    the first resistive load and the second resistive load being adjustable so as to increase modeling accuracy of the homeostatic model circuit.

4. The apparatus of claim 1, the circadian model circuit providing an oscillatory output including a first component having a period of approximately 12 hours, and a second component having a period of approximately 24 hours.

5. The apparatus of claim 4, the electronic circuit further comprising a phase shift adjustment circuit operable to modify relative phases of the first component and the second component.

6. The apparatus of claim 5, further comprising a light sensor providing a light sensor signal,
the phase shift adjustment circuit receiving the light sensor signal,
the relative phases of the first component and the second component being adjustable in response to the light sensor signal.

7. The apparatus of claim 5, further comprising a position sensor providing a position signal,
the phase shift adjustment circuit receiving the position signal,
the relative phases of the first component and the second component being adjustable in response to position signal.

8. The apparatus of claim 5, the oscillatory output including a third component,
the amplitude and relative phase of the third component being adjustable so as to improve accuracy of the circadian model circuit.

9. The apparatus of claim 1, further comprising a visual indicator for displaying the alertness.

10. The apparatus of claim 9, wherein the visual indicator is an electronic display.

11. The apparatus of claim 1, further comprising an audible alarm,
the audible alarm being energized when the alertness falls below a threshold value.

12. The apparatus of claim 1, further comprising a sleep-wake transition detection circuit,
the sleep-wake transition detection circuit receiving a sensor signal from a sensor,
the sleep-wake transition detection circuit being operable to detect transitions between a sleeping state and a waking state using the sensor signal.

13. The apparatus of claim 12, the electronic circuit including at least one switch responsive to transitions detected by the sleep-wake transition detection circuit.

14. The apparatus of claim 12, the sensor being an activity sensor.

15. The apparatus of claim 12, the sensor being a light sensor.

16. The apparatus of claim 1, the apparatus comprising a memory, sleep-wake transitions being associated with transition times, the transition times being stored in the memory.

17. The apparatus of claim 16, the apparatus comprising a data input mechanism, the transition times being input using the data input mechanism.

18. The apparatus of claim 16, the apparatus using temporal scaling to estimate the alertness.

19. The apparatus of claim 18, the apparatus being operable to provide an alertness estimate for a future time using the transition times stored in the memory.

20. The apparatus of claim 19, the homeostatic model circuit and the circadian model circuit using a temporal scaling parameter of at least 10,000, thereby providing modeling at least 10,000 times faster than real time simulation.

21. An apparatus for determining an alertness given a sleep-wake cycle having a homeostatic component, the apparatus comprising:
an electronic circuit including:
a circadian model circuit configured to model the circadian component, and
a homeostatic model circuit configured to model the homeostatic component of the sleep-wake cycle,
the homeostatic model circuit including a resistor-capacitor analog circuit having a capacitive element,
the capacitive element being charged through a first resistive load and discharged through a second resistive load,
the homeostatic component being modeled using a potential difference across the capacitive element,
the resistor-capacitor analog circuit further including at least one switch responsive to a sleep-wake transition signal.

22. The apparatus of claim 21, wherein the electronic circuit further includes an inertial model circuit configured to model an inertial component of the sleep-wake cycle,
the inertial model circuit including a resistor-inductor analog circuit having an inductive element,
the inductive element being energized through a first inertial model resistive load and discharged through a second inertial model resistive load,
the inertial component being modeled by a potential difference across the inductive element,
the resistor-inductor analog circuit further including at least one inertial model switch responsive to the sleep-wake transition signal,
the electronic circuit being operable to combine outputs from the homeostatic model circuit, the inertial model circuit, and the circadian model circuit so as to estimate the alertness.

23. The apparatus of claim 21, the sleep-wake transition signal being provided by a sleep-wake transition detection circuit.

24. A method of determining an alertness of a living being, the living being having a sleep-wake cycle having a homeostatic component and a circadian component, the method comprising:
modeling the circadian component using a circadian model circuit;
modeling the homeostatic component using a homeostatic model circuit, the homeostatic model circuit being a resistor-capacitor analog circuit; and
combining outputs of the homeostatic model circuit and the circadian model circuit so as to estimate the alertness.

25. The method of claim 24, the sleep-wake cycle further comprising an inertial component, the method further comprising:
modeling the inertial component using an inertial model circuit including a resistor-inductor analog circuit,
the alertness being estimated by combining outputs from the circadian model circuit, homeostatic modeling circuit and the inertial modeling circuit.

26. The method of claim 24, further including determining sleep-wake transition data,
the homeostatic model circuit including at least one switch responsive to the sleep-wake transition data.

27. The method of claim 24, further comprising use of temporal scaling to speed up the alertness estimate,
the homeostatic modeling circuit, the inertial modeling circuit, and the circadian model circuit using one second or less to represent one hour of the sleep-wake cycle.

* * * * *